(12) United States Patent
Bachmann et al.

(10) Patent No.: US 8,759,494 B2
(45) Date of Patent: Jun. 24, 2014

(54) ANTI-CD33 ANTIBODIES AND USE THEREOF FOR IMMUNOTARGETING IN TREATING CD33-ASSOCIATED ILLNESSES

(75) Inventors: Michael Bachmann, Kelkheim (DE); Slava Stamova, Karlsruhe (DE)

(73) Assignee: GEMoaB Monoclonals GmbH, Dresden (DE)

( * ) Notice: Subject to any disclaimer, the term of this patent is extended or adjusted under 35 U.S.C. 154(b) by 0 days.

(21) Appl. No.: 13/497,800

(22) PCT Filed: Sep. 22, 2010

(86) PCT No.: PCT/EP2010/063990
§ 371 (c)(1),
(2), (4) Date: Jun. 7, 2012

(87) PCT Pub. No.: WO2011/036183
PCT Pub. Date: Mar. 31, 2011

(65) Prior Publication Data
US 2012/0251554 A1    Oct. 4, 2012

(30) Foreign Application Priority Data

Sep. 25, 2009  (DE) .......................... 10 2009 045 006

(51) Int. Cl.
| C07K 16/00 | (2006.01) |
| C12P 21/08 | (2006.01) |
| C07H 21/04 | (2006.01) |
| C12N 15/00 | (2006.01) |
| C12P 21/04 | (2006.01) |
| C12N 1/12 | (2006.01) |

(52) U.S. Cl.
USPC ................. 530/388.1; 530/387.3; 530/391.1; 536/23.53; 435/320.1; 435/69.6; 435/252.1

(58) Field of Classification Search
None
See application file for complete search history.

(56) References Cited

U.S. PATENT DOCUMENTS

| 5,730,982 A | 3/1998 | Scheinberg |
| 7,557,189 B2 | 7/2009 | Hoffee et al. |

FOREIGN PATENT DOCUMENTS

| CN | 101 210 048 A | 7/2008 |
| EP | 1656950 A1 | 5/2006 |
| WO | 2004/043344 A2 | 5/2004 |

OTHER PUBLICATIONS

Overbeek, 1994, "Factors affecting transgenic animal production," Transgenic animal technology, pp. 96-98.*
Wall, 1996 Theriogenology, vol. 45, pp. 57-68.*
Houdebine, 1994, J. Biotech. vol. 34, pp. 269-287, specifically p. 281.*
Kappell, 1992, Current Opinions in Biotechnology, vol. 3, pp. 548-553.*
Cameron, 1997, Mol. Biol. 7, pp. 253-265.*
Mullins, 1993, Hypotension, vol. 22, pp. 630-633.*
Mullins, 1990, Nature, vol. 344, 541-544.*
Hammer, 1990, Cell, vol. 63, 1099-1112.*
Niemann, 1997, Transg. Res. 7, pp. 73-75.*
Mullins, 1989, EMBO J., vol. 8, pp. 4065-4072.*
Taurog, 1988, J. Immunol., vol. 141, pp. 4020-4023.*
Mullins,1996, J. Clin. Invest. vol. 98, pp. S37-S40.*
Feldman J. et al.: Phase III Randomized Multicenter Study of a Humanized Anti-CD33 Monoclonal Antibody, Lintuzumab, in Combination With Chemotherapy, Versus Chemotherapy Alone in Patients With Refractory or First-Relapsed Acute Myeloid Leukemia. J. Clin. Oncol. 23 (18) 2005, pp. 4110-4116.
Bauerle P. A. et al.: BiTE: Teaching antibodies to engage T cells for cancer therapy. Curr Opin Mol Ther 11, 2009, pp. 22-30.
Bargou R. et al.: Tumor regression in cancer patients by very low doses of a T cell-engaging antibody. Science 321, 2008, pp. 974-977.
Brischwein K. et al.: MT110: a novel bispecific single-chain antibody construct with high efficacy in eradicating established tumors. Mol Immunol 43, 2006, pp. 1129-1143.
Walter R. B. et al.: Influence of CD33 expression levels and ITIM-dependent internalization on gemtuzumab ozogamicin-induced cytotoxicity; Blood; Feb. 1, 2005; vol. 105 No. 3, pp. 1295-1302.
Linenberger M. L.: CD33-directed therapy with gemtuzumab ozogamicin in acute myeloid leukemia: progress in understanding cytotoxicity and potential mechanisms of drug resistance; Leukemia: Official Journal of the Leukemia Society of America, Leukemia Research Fund; UK, Feb. 2005; vol. 19, No. 2; pp. 176-182.
Kobayashi Yukio et al.: Phase I/II study of humanized anti-CD33 antibody conjugated with calichemeamicin , gemtuzumab ozogamizin, in relapsed or refractory acute myeloid leukemia: final results of Japanese multicenter cooperative study; International Journal of Hematology ; May 2009; vol. 89, No. 4; pp. 460-469.

(Continued)

*Primary Examiner* — Hong Sang
(74) *Attorney, Agent, or Firm* — Gudrun E. Huckett

(57) ABSTRACT

The invention relates to antibodies to the tumor-associated antigen CD33 and to the use thereof for immunotargeting CD33-positive cells. The antibodies according to the invention are suitable for use in the field of medicine, pharmaceuticals, and biomedical research. According to the invention, the aim is achieved by means of novel anti-CD33 antibodies comprising the complementary determining regions (CDRs) defined in the claim. The antibodies according to the invention are characterized by a high affinity for human CD33, of the order of magnitude of $10^{-10}$ mol/l. The CDR sequences according to the invention are suitable in particular for producing recombinant fragments (such as scFv fragments or bispecific antibodies) and for immunotargeting, due to the high affinity thereof. The invention further relates to the use of an antibody according to the invention for producing a medication for therapeutic and/or diagnostic application for illnesses associated with the expression of CD33, particularly for acute myeloid leukemia (AML). The invention thus also comprises a pharmaceutical composition comprising one or more antibodies according to the invention in association with a pharmaceutically acceptable thinning agent or carrier.

14 Claims, 7 Drawing Sheets

(56) References Cited

OTHER PUBLICATIONS

Lamba J. K. et al.: Coding polymorphism in CD33 and responses to gemtuzumab ozogamicin in pedriatic patients with AML: a pilot study; Leukemia: Official Journal of the Leukemia Society of America, Leukemia Research Fund; UK, Feb. 2009; vol. 23, No. 2; pp. 402-404.

Wellhausen S. R. et al.: CD33: Biochemical and Biological Characterization and Evaluation of Clinical Relevance; Journal of Biological Regulators and Homeostatic Agents; Wichtig Editore, Milan IT; vol. 16, No. 2, Jan. 1, 2002; pp. 139-143.

Lehmann S.: Bifunktionelle Proteine zum Reprogammieren des Immunsystems; Jan. 23, 2008; XP002612909 (see international search report).

Walter R. B.: Mechanism of endocytosis of CD33/Siglec-3: Role of ITIMs, tyrosine phosphorylation, and monoubiquitylation; Thesis, University od Washington, May 2007; XP002612910 (see international search report).

Riudikoff S. et al.: Single amino acid substitution altering antigen-binding specificity; Proceedings of the National Academy of Sciences of the United States (PNAS), National Academy of Science, US; vol. 79, Mar. 1, 1982; pp. 1979-1983.

\* cited by examiner

| anti-CD33 DRB1 | V_H CDR1 | SEQ ID | %SI | V_H CDR2 | SEQ ID | %SI | V_H CDR3 | SEQ ID | %SI |
|---|---|---|---|---|---|---|---|---|---|
|  | DYVLH | 7 |  | GLINTYNGDVEYNQKFMGK | 35 |  | DYRYEYYAMDY | 9 |  |
| US 7,557,189 | SYYIH | 37 | 40 | VIYPGNDDISYNQKFKS | 38 | 66 | EVRLRYFDV | 39 | 11 |
| US 5,730,982 | DYNMH | 43 | 60 | YIYPYNGGTGYNQKFKS | 44 | 72 | GRP----AMDY | 45 | 36 |
| CN101210048 | DYNMY | 49 | 40 | GYIDPYKGGTIYNQKFKG | 55 | 56 | Q-MITAYYFDY | 51 | 27 |
| anti-CD33 DRB2 | DYVVH | 1 |  | YINPYNDGTKYNEKFKG | 2 |  | DYRYEYYGMDY | 3 |  |
| US 7,557,189 | SYYIH | 37 | 40 | VIYPGNDDISYNQKFKS | 38 | 58 | EVRLRYFDV | 39 | 11 |
| US 5,730,982 | DYNMH | 43 | 60 | YIYPYNGGTGYNQKFKS | 44 | 75 | GRP----AMDY | 45 | 27 |
| CN101210048 | DYNMY | 49 | 40 | GYIDPYKGGTIYNQKFKG | 55 | 70 | Q-MITAYYFDY | 51 | 27 |

| anti-CD33 DRB1 | V_L CDR1 | SEQ ID | %SI | V_L CDR2 | SEQ ID | %SI | V_L CDR3 | SEQ ID | %SI |
|---|---|---|---|---|---|---|---|---|---|
|  | SA-----NSSVS-YIH | 10 |  | DTSKLAS | 36 |  | QQWTSHPLT | 12 |  |
| US 7,557,189 | KSSQSVFFS----SSQKN-YLA | 40 | 20 | WASTRES | 41 | 66 | HQYLSSRT | 42 | 25 |
| US 5,730,982 | RASESVDNYGISFMN | 46 | 20 | ASNQGS | 47 | 33 | QQSKEVPWT | 48 | 44 |
| CN101210048 | KA-----SQDINKYIA | 52 | 27 | TSTLQP | 53 | 33 | LQYDNL-LT | 54 | 33 |
| anti-CD33 DRB2 | TASSSVN------YIH | 4 |  | TSKVAS | 5 |  | QQWRSYFLT | 6 |  |
| US 7,557,189 | KSSQSVFFSSQKN-----YLA | 40 | 71 | WASTRES | 41 | 66 | HQYLSSRT | 42 | 25 |
| US 5,730,982 | RASESVDNYGISFMN | 46 | 75 | ASNQGS | 47 | 33 | QQSKEVPWT | 48 | 44 |
| CN101210048 | KASQDINK-----YIA | 52 | 36 | TSTLQP | 53 | 33 | LQYDNL-LT | 54 | 33 |

Fig. 1

SEQUENCE LISTING

```
<160> NUMBER OF SEQ ID NOS: 55

<210> SEQ ID NO 1
<211> LENGTH: 5
<212> TYPE: PRT
<213> ORGANISM: Mus musculus

<400> SEQUENCE: 1

Asp Tyr Val Val His
1               5

<210> SEQ ID NO 2
<211> LENGTH: 17
<212> TYPE: PRT
<213> ORGANISM: Mus musculus

<400> SEQUENCE: 2

Tyr Ile Asn Pro Tyr Asn Asp Gly Thr Lys Tyr Asn Glu Lys Phe Lys
1               5                   10                  15

Gly

<210> SEQ ID NO 3
<211> LENGTH: 11
<212> TYPE: PRT
<213> ORGANISM: Mus musculus

<400> SEQUENCE: 3

Asp Tyr Arg Tyr Glu Val Tyr Gly Met Asp Tyr
1               5                   10

<210> SEQ ID NO 4
<211> LENGTH: 10
<212> TYPE: PRT
<213> ORGANISM: Mus musculus

<400> SEQUENCE: 4

Thr Ala Ser Ser Ser Val Asn Tyr Ile His
1               5                   10

<210> SEQ ID NO 5
<211> LENGTH: 6
<212> TYPE: PRT
<213> ORGANISM: Mus musculus

<400> SEQUENCE: 5

Thr Ser Lys Val Ala Ser
1               5

<210> SEQ ID NO 6
<211> LENGTH: 9
<212> TYPE: PRT
<213> ORGANISM: Mus musculus

<400> SEQUENCE: 6

Gln Gln Trp Arg Ser Tyr Pro Leu Thr
1               5

<210> SEQ ID NO 7
```

```
<211> LENGTH: 5
<212> TYPE: PRT
<213> ORGANISM: Mus musculus

<400> SEQUENCE: 7

Asp Tyr Val Leu His
1               5

<210> SEQ ID NO 8
<211> LENGTH: 17
<212> TYPE: PRT
<213> ORGANISM: Mus musculus

<400> SEQUENCE: 8

Leu Ile Asn Thr Tyr Asn Gly Asp Val Arg Tyr Asn Gln Lys Phe Met
1               5                   10                  15

Gly

<210> SEQ ID NO 9
<211> LENGTH: 11
<212> TYPE: PRT
<213> ORGANISM: Mus musculus

<400> SEQUENCE: 9

Asp Tyr Arg Tyr Glu Tyr Tyr Ala Met Asp Tyr
1               5                   10

<210> SEQ ID NO 10
<211> LENGTH: 10
<212> TYPE: PRT
<213> ORGANISM: Mus musculus

<400> SEQUENCE: 10

Ser Ala Asn Ser Ser Val Ser Tyr Ile His
1               5                   10

<210> SEQ ID NO 11
<211> LENGTH: 6
<212> TYPE: PRT
<213> ORGANISM: Mus musculus

<400> SEQUENCE: 11

Thr Ser Lys Leu Ala Ser
1               5

<210> SEQ ID NO 12
<211> LENGTH: 9
<212> TYPE: PRT
<213> ORGANISM: Mus musculus

<400> SEQUENCE: 12

Gln Gln Trp Thr Ser His Pro Leu Thr
1               5

<210> SEQ ID NO 13
<211> LENGTH: 120
<212> TYPE: PRT
<213> ORGANISM: Mus musculus

<400> SEQUENCE: 13

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
            20                  25                  30
```

```
Val Val His Trp Leu Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
                100                 105                 110

Gly Thr Ser Val Thr Val Ser Ser
            115                 120

<210> SEQ ID NO 14
<211> LENGTH: 115
<212> TYPE: PRT
<213> ORGANISM: Mus musculus

<400> SEQUENCE: 14

Asp Ile Val Leu Thr Gln Ser Pro Thr Ile Met Ser Ala Ser Pro Gly
1               5                   10                  15

Glu Arg Val Thr Met Thr Cys Thr Ala Ser Ser Ser Val Asn Tyr Ile
            20                  25                  30

His Trp Tyr Gln Gln Lys Ser Gly Asp Ser Pro Lys Arg Trp Ile Phe
        35                  40                  45

Asp Thr Ser Lys Val Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Arg Ser Tyr Pro Leu Thr
                85                  90                  95

Phe Gly Asp Gly Thr Arg Leu Glu Leu Lys Arg Ala Asp Ala Ala Pro
                100                 105                 110

Thr Val Ser
        115

<210> SEQ ID NO 15
<211> LENGTH: 120
<212> TYPE: PRT
<213> ORGANISM: Mus musculus

<400> SEQUENCE: 15

Glu Val Lys Leu Gln Glu Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Val Leu His Trp Val Lys Gln Ser His Ala Lys Ser Leu Glu Trp Ile
        35                  40                  45

Gly Leu Ile Asn Thr Tyr Asn Gly Asp Val Arg Tyr Asn Gln Lys Phe
    50                  55                  60

Met Gly Lys Ala Thr Met Thr Ile Glu Lys Ser Ser Thr Ala Tyr
65                  70                  75                  80

Met Glu Leu Val Arg Leu Thr Ser Glu Asp Ser Ala Ile Tyr Tyr Cys
                85                  90                  95

Ala Arg Asp Tyr Arg Tyr Glu Tyr Tyr Ala Met Asp Tyr Trp Gly Gln
                100                 105                 110
```

```
<210> SEQ ID NO 16
<211> LENGTH: 115
<212> TYPE: PRT
<213> ORGANISM: Mus musculus

<400> SEQUENCE: 16

Asp Ile Val Leu Thr Gln Ser Pro Ala Ile Met Ser Ala Ser Pro Gly
1               5                   10                  15
Glu Lys Val Thr Met Thr Cys Ser Ala Asn Ser Ser Val Ser Tyr Ile
            20                  25                  30
His Trp Tyr Gln Gln Lys Ser Gly Thr Ser Pro Lys Arg Trp Ile Phe
        35                  40                  45
Asp Thr Ser Lys Leu Ala Ser Gly Val Pro Ala Arg Phe Ser Gly Ser
    50                  55                  60
Gly Ser Gly Thr Ser Tyr Ser Leu Thr Ile Ser Thr Met Glu Ala Glu
65                  70                  75                  80
Asp Ala Ala Thr Tyr Tyr Cys Gln Gln Trp Thr Ser His Pro Leu Thr
                85                  90                  95
Phe Gly Thr Gly Thr Lys Leu Gln Leu Lys Arg Ala Asp Ala Ala Pro
            100                 105                 110
Thr Val Ser
        115

<210> SEQ ID NO 17
<211> LENGTH: 15
<212> TYPE: DNA
<213> ORGANISM: Mus musculus

<400> SEQUENCE: 17
gactatgttg tgcac                                                    15

<210> SEQ ID NO 18
<211> LENGTH: 51
<212> TYPE: DNA
<213> ORGANISM: Mus musculus

<400> SEQUENCE: 18
tatattaatc cttacaatga tggtactaag tacaatgaga agttcaaagg c             51

<210> SEQ ID NO 19
<211> LENGTH: 33
<212> TYPE: DNA
<213> ORGANISM: Mus musculus

<400> SEQUENCE: 19
gactataggt acgaggtcta tggtatggac tac                                33

<210> SEQ ID NO 20
<211> LENGTH: 30
<212> TYPE: DNA
<213> ORGANISM: Mus musculus

<400> SEQUENCE: 20
actgccagct caagtgtaaa ttacatacac                                    30

<210> SEQ ID NO 21
<211> LENGTH: 21
```

<210> SEQ ID NO 21
<211> LENGTH: 21
<212> TYPE: DNA
<213> ORGANISM: Mus musculus

<400> SEQUENCE: 21
gacacatcca aagtggcttc t                                      21

<210> SEQ ID NO 22
<211> LENGTH: 27
<212> TYPE: DNA
<213> ORGANISM: Mus musculus

<400> SEQUENCE: 22
cagcagtggc gaagttaccc tctcacg                                27

<210> SEQ ID NO 23
<211> LENGTH: 15
<212> TYPE: DNA
<213> ORGANISM: Mus musculus

<400> SEQUENCE: 23
gattatgttt tacac                                             15

<210> SEQ ID NO 24
<211> LENGTH: 51
<212> TYPE: DNA
<213> ORGANISM: Mus musculus

<400> SEQUENCE: 24
cttattaata cttataatgg tgacgttagg tacaaccaga agttcatggg c      51

<210> SEQ ID NO 25
<211> LENGTH: 33
<212> TYPE: DNA
<213> ORGANISM: Mus musculus

<400> SEQUENCE: 25
gactataggt acgaatacta tgctatggac tac                         33

<210> SEQ ID NO 26
<211> LENGTH: 30
<212> TYPE: DNA
<213> ORGANISM: Mus musculus

<400> SEQUENCE: 26
agtgccaact caagtgtcag ttacatacac                             30

<210> SEQ ID NO 27
<211> LENGTH: 18
<212> TYPE: DNA
<213> ORGANISM: Mus musculus

<400> SEQUENCE: 27
acatccaaac tggcttct                                          18

<210> SEQ ID NO 28
<211> LENGTH: 27
<212> TYPE: DNA
<213> ORGANISM: Mus musculus

<400> SEQUENCE: 28
cagcagtgga ctagtcaccc actcacg                                27

<210> SEQ ID NO 29

<211> LENGTH: 360
<212> TYPE: DNA
<213> ORGANISM: Mus musculus

<400> SEQUENCE: 29

```
gaggtcaagc tgcaggagtc aggacctgag ctggtaaagc ctggggcttc agtgaagatg    60
tcctgcaagg cttctggata caaattcact gactatgttg tgcactggct gaagcagaag   120
cctgggcagg gccttgagtg gattggatat attaatcctt acaatgatgg tactaagtac   180
aatgagaagt tcaaaggcaa ggccacactg acttcagaca aatcctccag cacagcctac   240
atggaggtca gcagcctgac ctctgaggac tctgcggtct attattgtgc aagagactat   300
aggtacgagg tctatggtat ggactactgg ggtcaaggaa cctcagtcac cgtctcctca   360
```

<210> SEQ ID NO 30
<211> LENGTH: 345
<212> TYPE: DNA
<213> ORGANISM: Mus musculus

<400> SEQUENCE: 30

```
gacattgtgc tgacccagtc tccaacaatc atgtctgcat ctccagggga gagggtcacc    60
atgacctgca ctgccagctc aagtgtaaat tacatatact ggtaccagca gaagtcaggc   120
gactccccca aaagatggat tttcgacaca tccaaagtgg cttctggagt ccctgctcgc   180
ttcagtggca gtgggtcagg gacctcttac tctctcacaa tcagtaccat ggaggctgaa   240
gatgctgcca cttattactg ccagcagtgg cgaagttacc ctctcacgtt cggtgatggg   300
accaggctgg agctgaaacg ggctgatgct gcaccaactg tatcc                   345
```

<210> SEQ ID NO 31
<211> LENGTH: 360
<212> TYPE: DNA
<213> ORGANISM: Mus musculus

<400> SEQUENCE: 31

```
gaggtcaagc tgcaggagtc aggggctgag ctggtgaggc ctggggtctc agtgaagatc    60
tcctgcaagg gttctggcta cacattcact gattatgttt tacactgggt gaagcagagt   120
catgcaaaga gtctagagtg gattggactt attaatactt ataatggtga cgttaggtac   180
aaccagaagt tcatgggcaa ggccacaatg accatagaga atcctccag cacagcctat    240 atggaacttg tcagactgac atctgaggat tctgccatct attactgtgc aagagactat   300
aggtacgaat actatgctat ggactactgg ggtcaaggaa cttcagtcac cgtctcctca   360
```

<210> SEQ ID NO 32
<211> LENGTH: 345
<212> TYPE: DNA
<213> ORGANISM: Mus musculus

<400> SEQUENCE: 32

```
gacattgtgc tgacccagtc tccagcaatc atgtctgcat ctccagggga gaaggtcacc    60
atgacctgca gtgccaactc aagtgtcagt tacatacact ggtaccagca gaagtcaggc   120
acttccccca aaagatggat ttttgacaca tccaaactgg cttctggagt ccctgctcgc   180
ttcagtggca gtgggtctgg gacctcttac tctctcacaa tcagcaccat ggaggctgaa   240
gatgctgcca cttattactg ccagcagtgg actagtcacc cactcacgtt cggtactggg   300
accaagctgc agctgaaacg ggctgatgct gcaccaactg tatcc                   345
```

```
<210> SEQ ID NO 33
<211> LENGTH: 18
<212> TYPE: PRT
<213> ORGANISM: Mus musculus

<400> SEQUENCE: 33

Gly Leu Ile Asn Thr Tyr Asn Gly Asp Val Arg Tyr Asn Gln Lys Phe
1               5                   10                  15

Met Gly

<210> SEQ ID NO 34
<211> LENGTH: 18
<212> TYPE: PRT
<213> ORGANISM: Mus musculus

<400> SEQUENCE: 34

Leu Ile Asn Thr Tyr Asn Gly Asp Val Arg Tyr Asn Gln Lys Phe Met
1               5                   10                  15

Gly Lys

<210> SEQ ID NO 35
<211> LENGTH: 19
<212> TYPE: PRT
<213> ORGANISM: Mus musculus

<400> SEQUENCE: 35

Gly Leu Ile Asn Thr Tyr Asn Gly Asp Val Arg Tyr Asn Gln Lys Phe
1               5                   10                  15

Met Gly Lys

<210> SEQ ID NO 36
<211> LENGTH: 7
<212> TYPE: PRT
<213> ORGANISM: Mus musculus

<400> SEQUENCE: 36

Asp Thr Ser Lys Leu Ala Ser
1               5

<210> SEQ ID NO 37
<211> LENGTH: 5
<212> TYPE: PRT
<213> ORGANISM: Mus musculus

<400> SEQUENCE: 37

Ser Tyr Tyr Ile His
1               5

<210> SEQ ID NO 38
<211> LENGTH: 17
<212> TYPE: PRT
<213> ORGANISM: Mus musculus
<220> FEATURE:
<221> NAME/KEY: misc_feature
<222> LOCATION: (16)..(16)
<223> OTHER INFORMATION: Xaa can be any naturally occurring amino acid

<400> SEQUENCE: 38

Val Ile Tyr Pro Gly Asn Asp Asp Ile Ser Tyr Asn Gln Lys Phe Xaa
1               5                   10                  15

Gly

<210> SEQ ID NO 39
```

```
<211> LENGTH: 9
<212> TYPE: PRT
<213> ORGANISM: Mus musculus

<400> SEQUENCE: 39

Glu Val Arg Leu Arg Tyr Phe Asp Val
1               5

<210> SEQ ID NO 40
<211> LENGTH: 17
<212> TYPE: PRT
<213> ORGANISM: Mus musculus

<400> SEQUENCE: 40

Lys Ser Ser Gln Ser Val Phe Phe Ser Ser Gln Lys Asn Tyr Leu
1               5                   10                  15

Ala

<210> SEQ ID NO 41
<211> LENGTH: 7
<212> TYPE: PRT
<213> ORGANISM: Mus musculus

<400> SEQUENCE: 41

Trp Ala Ser Thr Arg Glu Ser
1               5

<210> SEQ ID NO 42
<211> LENGTH: 8
<212> TYPE: PRT
<213> ORGANISM: Mus musculus

<400> SEQUENCE: 42

His Gln Tyr Leu Ser Ser Arg Thr
1               5

<210> SEQ ID NO 43
<211> LENGTH: 5
<212> TYPE: PRT
<213> ORGANISM: Mus musculus

<400> SEQUENCE: 43

Asp Tyr Asn Met His
1               5

<210> SEQ ID NO 44
<211> LENGTH: 17
<212> TYPE: PRT
<213> ORGANISM: Mus musculus

<400> SEQUENCE: 44

Tyr Ile Tyr Pro Tyr Asn Gly Gly Thr Gly Tyr Asn Gln Lys Phe Lys
1               5                   10                  15

Ser

<210> SEQ ID NO 45
<211> LENGTH: 7
<212> TYPE: PRT
<213> ORGANISM: Mus musculus

<400> SEQUENCE: 45

Gly Arg Pro Ala Met Asp Tyr
1               5
```

```
<210> SEQ ID NO 46
<211> LENGTH: 15
<212> TYPE: PRT
<213> ORGANISM: Mus musculus

<400> SEQUENCE: 46

Arg Ala Ser Glu Ser Val Asp Asn Tyr Gly Ile Ser Phe Met Asn
1               5                   10                  15

<210> SEQ ID NO 47
<211> LENGTH: 6
<212> TYPE: PRT
<213> ORGANISM: Mus musculus

<400> SEQUENCE: 47

Ala Ser Asn Gln Gly Ser
1               5

<210> SEQ ID NO 48
<211> LENGTH: 9
<212> TYPE: PRT
<213> ORGANISM: Mus musculus

<400> SEQUENCE: 48

Gln Gln Ser Lys Glu Val Pro Trp Thr
1               5

<210> SEQ ID NO 49
<211> LENGTH: 5
<212> TYPE: PRT
<213> ORGANISM: Mus musculus

<400> SEQUENCE: 49

Asp Tyr Asn Met Tyr
1               5

<210> SEQ ID NO 50
<211> LENGTH: 17
<212> TYPE: PRT
<213> ORGANISM: Mus musculus

<400> SEQUENCE: 50

Tyr Ile Asp Pro Tyr Lys Gly Gly Thr Ile Tyr Asn Gln Lys Phe Lys
1               5                   10                  15

Gly

<210> SEQ ID NO 51
<211> LENGTH: 10
<212> TYPE: PRT
<213> ORGANISM: Mus musculus

<400> SEQUENCE: 51

Gln Met Ile Thr Ala Tyr Tyr Phe Asp Tyr
1               5                   10

<210> SEQ ID NO 52
<211> LENGTH: 11
<212> TYPE: PRT
<213> ORGANISM: Mus musculus

<400> SEQUENCE: 52

Lys Ala Ser Gln Asp Ile Asn Lys Tyr Ile Ala
1               5                   10
```

```
<210> SEQ ID NO 53
<211> LENGTH: 6
<212> TYPE: PRT
<213> ORGANISM: Mus musculus

<400> SEQUENCE: 53

Thr Ser Thr Leu Gln Pro
1               5

<210> SEQ ID NO 54
<211> LENGTH: 8
<212> TYPE: PRT
<213> ORGANISM: Mus musculus

<400> SEQUENCE: 54

Leu Gln Tyr Asp Asn Leu Leu Thr
1               5

<210> SEQ ID NO 55
<211> LENGTH: 18
<212> TYPE: PRT
<213> ORGANISM: Mus musculus

<400> SEQUENCE: 55

Gly Tyr Ile Asp Pro Tyr Lys Gly Gly Thr Ile Tyr Asn Gln Lys Phe
1               5                   10                  15

Lys Gly
```

ANTI-CD33 ANTIBODIES AND USE THEREOF FOR IMMUNOTARGETING IN TREATING CD33-ASSOCIATED ILLNESSES

BACKGROUND OF THE INVENTION

The invention concerns antibodies against the tumor-associated antigen CD33 and their use for immunotargeting of CD33-positive cells. The antibodies according to the invention are suitable for use in the medical field, in pharmacy and in biomedical research.

Cancer (malignant neoplasia) is a class of illnesses in which a group of cells is characterized by uncontrolled cell division, by invasion into and destruction of adjoining tissues and sometimes also by metastasis. These malignant properties of cancer differentiate it from benign tumors which, by their growth, displace surrounding tissue but do not infiltrate it and do not metastasize. Most cancer types form tumors, some do not, such as leukemia that affects the hematopoietic system. Cancer in the context of the invention refers to malignant tumors as well as to hemoblastoses.

In cancer cells, the adjustment of growth, division, and destruction in the united cell structure is not functioning. They are generated when certain genes change, these changes are no longer repaired, leading to non-functionality of certain gene regions, so that the cancer cells stimulate themselves to undergo division and ignore growth-inhibiting signals of the cell environment.

In principle, the immune system attempts to fight the uncontrolled growth of the cells. Problematic in this context is the fact that cancer cells are similar to normal body cells in many respects because they have evolved from them. Therefore, the defense measures of the immune system are usually not sufficient in order to control growth of the tumor.

In case of acute myeloid leukemia (AML), the myelopoiesis is affected, i.e., the part of the hematopoietic system that is responsible for the formation of granulocytes and monocytes. The myeloblasts represent in hematopoiesis an immature precursor of the myeloid white blood cells. In AML, several genetic modifications that concern the genes responsible for cell division result in a single myeloblast for formation of a cell that remains in the immature state and proliferates massively. This proliferation of the immature precursors in the bone marrow and also in the blood characterizes AML.

The modifications may be realized at several positions of the cell cycle so that AML has different phenotypic, genotypic and clinical properties. Modern classification of AML is based on the thesis that the properties and behavior of the tumor cells depend on at which stage of the cell cycle the proliferation was stopped. In many AML patients certain specific cytogenetic distinctive features can be determined which are often of prognostic significance. The genetic modifications code for abnormal fusion proteins, mostly transcription factors, causing the uncontrolled proliferation.

Tumor cells differ from healthy cells by the expression of tumor antigens, i.e., of proteins that are expressed only by the tumor cells. They are generated as a result of the modified genome in the cancer cells, i.e., by modified gene expression. Tumor antigens are located on the external cell membrane of the tumor cells, in the cell plasma, and in the cell nucleus. The tumor antigens as a target structure are the basis for most of the concepts of cancer immunotherapy. Currently, more than 2,000 tumor antigens are known.

Ideal as a target for the cancer therapy are tumor-specific antigens (TSA). i.e., antigens produced only by cancer cells but not by healthy cells. Most tumor antigens are however not tumor-specific but tumor-associated (TAA), i.e., they are also expressed by healthy cells. However, in many tumors the tumor antigens are overexpressed. By mutations in the genome, structural changes in the protein sequence can occur also. Many tumor antigens occur only for certain tumor types and, in this connection, often only in certain situations.

Tumor antigens that are present in case of AML comprise inter alia TAAs that are associated with a series of further tumor illnesses, for example, telomerase reverse transcriptase, Wilm's tumor 1 (WT1)-protein, and survivin. Moreover, there are also TAAs known that are associated with other leukemia illnesses such as CD168 and M phase phosphoprotein. Moreover, there are TAAs found in particular in connection with AML, such as CD33, CD45 and mHAgs (minor histocompatibility antigen).

CD33 is a glycosylated transmembrane protein of 364 amino acids and belongs to the family of sialic acid binding Ig-related lectins (SIGLECs). It is expressed also in early hematopoietic precursor cells, myelomonocytic precursors, and myeloid cells while it is not present on normal pluripotent bone marrow stem cells. Approximately 85-90% of AML patients are positive with regard to CD33. Therefore, CD33 is a particularly attractive target for immunotherapy and is already used as a target in a targeted immunotherapy.

The conventional AML therapy is a chemotherapy for induction of remission; subsequently, this may be followed by several chemotherapies or transplantation of hematopoietic stem cells. In the United States, a monoclonal antibody conjugated with a cytostatic agent, gemtuzumab ozogamicin, was approved in the year 2000 for patients with recurrent AML who are no candidates for the standard chemotherapy.

Antibodies are proteins of the class of globulins which in vertebrates are formed in response to certain substances, i.e., antigens. In combating cancer cells, the body's own polyclonal antibodies only play a very minor role. This results from the fact that most tumor cells do not present sufficiently strongly modified antigens that are recognized as foreign by the body's own immune system so that the body's own antibodies do not bind in a sufficient number to the tumor cells. Monoclonal antibodies are with respect to their structure completely identical and are specific to only one epitope of an antigen.

For cancer therapy, the employed monoclonal antibodies act almost exclusively by the antibody-dependent cell-mediated cytotoxicity (antibody dependent cellular cytotoxicity, ADCC). In this connection, antibodies recruit cytotoxic effector cells, such as NK cells, macrophages, lymphocytes or granulocytes that themselves have no antigen specificity, to the tumor cell by means of their Fc region. The direct damage of the cell by bound monoclonal antibodies, such as by triggering certain intracellular signal cascades that initiate apoptosis by cross-linking of the tumor antigens as a result of antibody binding, is a rare exception.

In order to reinforce the effect of monoclonal antibodies in cancer illnesses, different strategies of drug targeting have been developed in order to utilize the antibodies as carriers for more potent active ingredients, so-called immunoconjugates or antibody derivatives. For this purpose, active ingredients such as radionuclides, toxins (for example, the diphtheria toxin), cytokines or also cytostatic agents were bonded (conjugated) to the corresponding antibodies.

In this connection, it is in principle possible to bind highly potent active ingredients that, in case of free systemic administration would cause intolerable side effects as a result of their high toxicity, to an antibody. The antibody derivatives are comprised of three components: an antibody or antibody fragment, an active ingredient, and a linking member (linker) between antibody and active ingredient.

The first clinically tested antibody directed against CD33 is M195. The humanized variant of this antibody of the isotype IgGl, also known by the name lintuzumab, was tested in clinical studies wherein in phase III no advantage of lintuzumab in combination with chemotherapy was however determined when compared to chemotherapy alone (E. J. Feldman et. al., Phase III Randomized Multicenter Study of a Humanized Anti-CD33 Monoclonal Antibody, Lintuzumab, in Combination With Chemotherapy, Versus Chemotherapy Alone in Patients With Refractory or First-Relapsed Acute Myeloid Leukemia. J. Clin. Oncol. 23 (18) 2005, pp. 4110-4116).

Gemtuzumab ozogamicin is an immunoconjugate of the monoclonal antibody specific to CD33 of the type IgG4 that has been used in the USA for treatment of AML until 2010 but has been taken off the market in the meantime. It is comprised of a humanized monoclonal antibody against CD33 which is conjugated with a cytostatic agent, calicheamicin. The action mechanism is based on the endocytosis of the antibody derivative so that the cytostatic agent coupled thereto develops its toxic action after absorption in the cell. Gemtuzumab ozogamicin was not approved in Europe because the efficacy was not satisfactorily proven in the eyes of the European Medicines Agency EMEA.

The following table shows the amino acid sequences of the CDRs (complementary determining regions, the antigen binding sites of an antibody) of the anti-CD33 antibodies disclosed in the corresponding documents.

region. In this connection, generally an improved activation of the body's own immune cells relative to the tumor cells is achieved.

Bispecific antibodies of the newer generation are comprised of two different scFv fragments. They are connected to each other by a linker. For example, a bispecific antibody can bind with an scFv to tumor cells and with the other scFv to effector cells.

When a paratope is specific to T cells, these cells can be activated also. This is not possible with normal monoclonal antibodies because T cells have no Fc receptor. Bispecific antibodies have moreover a higher cytotoxic potential. They bind also to antigens that are expressed relatively weakly.

Up to now, no bispecific antibodies for clinical use in humans have been approved.

Bispecific antibodies are known in which an scFv binds to the CD3 complex on T cells; these are referred to also as BiTE (bispecific T cell engager) (P. A. Baeuerle et. al., BiTE: Teaching antibodies to engage T cells for cancer therapy. Curr Opin Mol Ther 11, 2009, pp. 22-30).

At the moment, two different BiTE antibodies are in clinical studies. Blinatumomab, an antibody that is specific to CD3 and CD19, is tested in patients in late phases of non-Hodgkin lymphoma and in patients with acute lymphoblast leukemia of the B cell series (B-ALL). MT110 is an antibody that is specific to CD3 and EpCAM (epithelial cell adhesion molecule) and is tested in patients with bronchial carcinoma

| Document | $V_H$ CDR1 | SEQ ID NO. | $V_H$ CDR2 | SEQ ID NO. | $V_H$ CDR3 | SEQ ID NO. |
|---|---|---|---|---|---|---|
| U.S. Pat. No. 7,557,189 | SYYIH | 37 | VIYPGNDDISYNQKFXG | 38 | EVRLRYFDV | 39 |
| U.S. Pat. No. 5,730,982 | DYNMH | 43 | YIYPYNGGTGYNQKFKS | 44 | GRPAMDY | 45 |
| CN101210048 | DYNMY | 49 | YIDPYKGGTIYNQKFKG | 50 | QMITAYYFDY | 51 |

| | $V_L$ CDR1 | | $V_L$ CDR2 | | $V_L$ CDR3 | |
|---|---|---|---|---|---|---|
| U.S. Pat. No. 7,557,189 | KSSQSVFFSSSQKNYLA | 40 | WASTRES | 41 | HQYLSSRT | 42 |
| U.S. Pat. No. 5,730,982 | RASESVDNYGISFMN | 46 | ASNQGS | 47 | QQSKEVPWT | 48 |
| CN101210048 | KASQDINKYIA | 52 | TSTLQP | 53 | LQYDNLLT | 54 |

A general problem for the therapeutic effectiveness of the monoclonal antibodies is the binding behavior of the antibodies on the cancer cells, i.e., the affinity of the antibodies. Even in cancer cells that present sufficient tumor antigens, the binding rate is often not satisfactorily high. With a molecular mass of approximately 150 kDa, antibodies are moreover generally limited in regard to their tissue migration. In this case, antibody fragments, such as Fab, F(ab)$_2$, or scFv (single chain variable fragments), have significant advantages as a result of their significantly reduced size.

Bispecific antibodies, i.e., antibody derivatives as components of two different monoclonal antibodies, provide new possibilities for therapy concepts in cancer immunotherapy.

Quadroma are bispecific antibodies of the first generation and are comprised each of a heavy chain and a light chain of two different monoclonal antibodies. The two arms of the antibody in this connection are specific to different antigens, respectively. The Fc region is formed commonly of the two heavy chains of the antibodies. By this configuration it is, for example, possible to place the paratope of an antibody specific to the tumor antigen and the paratope of another antibody specific to a lymphocyte antigen onto one arm each of the bispecific antibody. It is thus possible to form a three-cell complex that results from the respective different cells bonded to the paratopes and the effector cell bonded to the Fc and patients with gastrointestinal cancer illnesses (R. Bargou en. al., Tumor regression in cancer patients by very low doses of a T cell-engaging antibody. Science 321, 2008, pp. 974-977; K. Brischwein et. al., MT110: a novel bispecific single-chain antibody construct with high efficacy in eradicating established tumors. Mol Immunol 43, 2006, pp. 1129-1143).

Not all monoclonal antibodies are suitable in the form of scFv fragments or for the construction of bispecific constructs. In this connection, in particular the affinity of the antibodies is decisive that is determined by the variable regions. Only antibodies that have an especially high affinity are suitable as scFv fragments because binding to the respective antigen is realized only with one pair of variable regions of the heavy and light chains, in contrast to complete IgG antibodies that have two pairs of variable regions of the heavy and light chains.

For the treatment of AML and other carcinomas, there is the need for a new therapeutic concept. Antibodies that are currently known have an affinity that is too low for tumor-associated antigens such as CD33 in order to be usable therapeutically. Therefore, there is a need for the development of specific antibodies for tumor-associated antigens, for example, CD33, that have a high affinity and are therefore suitable for use in cancer therapy.

Object of the invention is therefore providing new anti-CD33 antibodies in particular with a high affinity to CD33 that enables use of the antibodies as recombinant fragments for immunotargeting.

SUMMARY OF THE INVENTION

According to the invention, the object is solved by new anti-CD33 antibodies which contain regions determined by complementarity (complementary determining regions, CDRs) that are characterized in that the CDRs of the variable region of the heavy chain ($V_H$) comprise the following sequences:
CDR1 SEQ ID NO. 01
CDR2 SEQ ID NO. 02
CDR3 SEQ ID NO, 03
and whose CDRs of the variable region of the light chain comprise the following sequences:
CDR1 SEQ ID NO. 04
CDR2 SEQ ID NO. 05
CDR3 SEQ ID NO. 06.

Especially preferred are anti-CD33 antibodies whose CDRs of the variable region of the heavy chain comprise the following sequences:
CDR1 SEQ ID NO. 07,
CDR2 SEQ ID NO. 08, or
  SEQ ID NO. 33, or
  SEQ ID NO. 34, or
  SEQ ID NO. 35,
CDR3 SEQ ID NO. 09
and whose CDRs of the variable region of the light chain comprise the following sequences:
CDR1 SEQ ID NO. 10,
CDR2 SEQ ID NO. 11 or SEQ ID NO. 36,
CDR3 SEQ ID NO. 12.

The anti-CD33 antibodies according to the invention, herein also referred to as anti-CD33DRB, are characterized by their amino acid sequences of the heavy and the light chains, their CDRs, and by methods for expression of the antibody in recombinant form.

Moreover, the anti-CD33DRB antibodies are functionally characterized and it has been demonstrated that they are distinguished by a high affinity for human CD33 (FIG. 3). The antibodies according to the invention have thus advantageously a high affinity for human CD33. The affinities of the native antibodies are within an order of magnitude of $10^{-10}$ mol/l. The affinities of the recombinant derivatives achieve $10^{-7}$ to $10^{-8}$ mol/l. It was possible to demonstrate that the antibodies predominately are not taken up by endocytosis in the CD33-positive cells and remain on the cell surface for a long period of time. This makes them particularly suitable for a therapeutic use for immunotargeting of effector cells on CD33-positive cells. Because of the high affinity the CDR sequences according to the invention are suitable in particular for preparing recombinant fragments (like scFv) and for immunotargeting.

The term antibody in the meaning of the invention comprises all antibodies, antibody fragments, and derivatives thereof that are capable of binding to the antigen, in this case CD33, that comprise the CDRs according to the invention completely or partially. This encompasses the complete monoclonal antibodies and also the epitope-binding fragments of these antibodies. In this connection, the epitope-binding fragments (also referred to herein as antibody fragments or antibody derivatives) comprise all regions of the antibody that are capable of binding to the antigen, in this case CD33. Examples of antibody fragments that are preferred in accordance with the invention comprise, but expressly are not limited to, Fab, Fab', F(ab')$_2$, Fd, individual chain (single-chain) variable fragments (scFv), single-chain antibodies, disulfide-linked variable fragments (sdFv), and fragments that either contain a variable region of the light chain ($V_L$) or a variable region of the heavy chain ($V_H$). Moreover, they include recombinantly prepared antibodies, such as diabodies, diabodies, and tetrabodies.

Preferably, the antibody carries a marker molecule, for example, biotin, dioxygenin, a radionuclide, or a fluorescent dye. Especially preferred, the antibody is conjugated with an effector group.

Antibody fragments contain the variable regions either alone or in combination with further regions that are selected from the hinge region and the first, second and third regions of the constant region ($C_H1$, $C_H2$, $C_H3$). Also, the term antibody comprises chimeric antibodies in which different regions of the antibody originate from different species, for example, antibodies with a murine variable region combined with a human constant region.

Antibody fragments are optionally linked with each other by a linker. The linker comprises a short (preferably 10 to 20 amino acid residues), flexible peptide sequence that is selected such that the antibody fragment has such a three-dimensional folding of $V_L$ and $V_H$ that it exhibits the antigen specificity of the complete antibody. Preferred linkers, but not exclusive linkers, are glycine-serine linkers with the structure $(Gly_xSer_y)$ with x and y selected from 1 to 10, preferably 3 to 5. Moreover, linkers are preferred that are comprised of a peptide sequence that can increase the protease resistance of the antibody derivatives.

The term variable region is defined in accordance with the invention as the regions of the heavy and light chains of the antibodies that differ in their sequence between antibodies and that determine the specificity of the antibody and binding to its antigen. The variability in this context is not distributed uniformly in the variable region. It is usually concentrated within three defined segments of the variable region that are referred to as complementary determining regions (CDRs) or also as hypervariable regions and are existing in the variable regions of the light as well as the heavy chains. The more strongly preserved portion of the variable regions are referred to as scaffolding regions (framework regions). The variable regions of the heavy and the light chains contain four framework regions that primarily assume a beta-sheet structure wherein each framework region is connected with three CDRs that form loops that connect the beta-sheet structures and in some cases are part of the beta-sheet structure. The CDRs of the respective chain are moved by the framework regions into immediate vicinity and contribute together with the CDRs of the other chain to the formation of the antigen binding region of the antibody.

The constant region (Fc) of the antibody is not participating in antigen binding but provides instead multiple effector functions that are triggered by binding to the corresponding Fc-binding receptors, for example, the induction of antibody-dependent cellular cytotoxicity (ADCC).

Preferably, the antibodies according to the invention comprise at least one variable region of the heavy chain ($V_H$) and a variable region of the light chain ($V_L$) in the form of an scFv. The variable region of the heavy chain ($V_H$) and the variable region of the light chain ($V_L$) each contain in this context at least one of the CDR sequences according to the invention.

According to the invention, antibodies are preferred that have the following structures that can be optionally humanized:
a variable region of the heavy chain according to sequence SEQ ID NO. 13 and a variable region of the light change according to sequence SEQ ID NO. 14.

Moreover, preferred antibodies are antibodies that contain the following structures:
a variable region of the heavy chain according to the sequence SEQ ID NO. 15 and a variable region of the light chain according to sequence SEQ ID NO. 16.

In the antibodies according to the invention, certain amino acids of the specific amino acid sequences can be exchanged in such a way that they maintain the binding properties of the CD33 antibody but differ in their sequence by exchange, deletion or addition of one or several amino acids. Therefore, encompassed are also antibodies that contain structures whose amino acid sequences relative to the amino acid sequences according to the invention of the variable regions according to SEQ ID NOs. 13 to 16 have a sequence identity of preferably at least 70%, especially preferred at least 80%, in particular at least 90%, and that bind the antigen CD33, wherein these sequences comprise at least one of the CDRs according to the invention in accordance with SEQ ID NOs. 1 to 12.

In preferred embodiments of the invention, the antibody comprises the following structures:
a variable region of the heavy chain with the sequence according to SEQ ID NO. 13 and a variable region of the light chain with the sequence according to SEQ ID NO. 14, or a variable region of the heavy chain with the sequence according to SEQ ID NO. 15 and a variable region of the light chain with the sequence according to SEQ ID NO. 16; and
a constant region of a heavy chain of a human IgG;
a region $C_L$ of the human kappa light chain
and a human IgG3 hinge region.

Optionally, the antibody is existing in the form of a F(ab')2 fragment.

In an especially preferred embodiment of the invention, antibodies are in the form of scFv fragments which contain at least one variable region of the heavy chain ($V_H$) and/or the variable region of the light chain ($V_L$) that contain the CDR regions according to the invention. Moreover, especially preferred are antibodies in the form of scFv fragments which comprise at least one of the variable regions of the heavy and/or light chain according to the invention.

The invention comprises murine anti-CD33 antibodies and humanized versions of these antibodies.

The goal of humanizing antibodies lies in the reduction of the immunogenicity of a xenogenic antibody, in this case of the murine antibody, for use in the human system wherein the complete binding affinity and the antigen specificity are maintained. Humanized antibodies can be prepared in various ways, for example, by resurfacing and CDR grafting. In case of resurfacing, by a combination of molecular modeling, statistic analyses, and mutagenesis, all non-CDR regions on the surface of the antibody are modified so that they are similar to the surface of antibodies of the target organism. In CDR grafting, the CDR regions according to the invention are introduced into human variable regions.

Humanized antibodies that contain the CDR regions according to the invention are expressly encompassed by the invention.

An aspect of the invention concerns also antibodies that are conjugated with an effector group. Conjugation in this context means the coupling of a substance to an antibody. The connection of the antibody to the effector group is preferably prepared by the expression as a fusion protein or by in vitro methods wherein the effector group preferably is bonded by a linker group to the antibody (for example, by means of thio-ether bonds or disulfide bonds). They may be bonded to the antibody also by an intermediary carrier molecule, for example, serum albumin. Optionally, an antibody contains also several effector groups.

In this connection, the effector groups are preferably pharmaceutically active substances (active ingredients). Preferred active ingredients comprise, but are not limited to, toxins, such as cytostatic agents, for example, maytansinoids and maytansinoid analogues, taxoids, CC-1065 and CC-1065 analogues, dolastatin and dolastatin analogues, methotrexate, daunorubicin, doxorubicin, vincristine, vinblastine, melphalan, mitomycin C, chlorambucil, and calicheamicin. The invention comprises also antibodies which are conjugated with radionuclides as effector groups and their use for therapy and diagnostics, in particular of tumors. Suitable radionuclides are preferably the radioactive isotopes of technetium, rhenium, yttrium, copper, gallium, indium, bismuth, and platinum, for example, $^{99m}$Tc, $^{90}$Y, $^{197}$Re, $^{188}$Re, $^{68}$Ga and $^{111}$In.

Effector groups according to the invention comprise furthermore enzymes (particularly enzymes suitable for the ADEPT system), co-stimulating molecules (e.g. CpG) or also nucleic acids. The antibody that is conjugated with an effector group may exist optionally in the form of a fusion protein.

Further aspects of the invention are also antibodies that are conjugated with a further antibody or antibody fragment which is specific to an antigen different than CD33. The antibody in this case is a bispecific antibody. Preferably, the antibody is a single chain bispecific diabody (scBsDb). In this case, two scFv fragments are connected to each other by means of a short linker (preferably having a length of 10 to 20 amino acid residues). It is preferred especially that the antibody is a single chain bispecific tandem antibody (scBsTaFv): In this case, the two scFv fragments are connected by a longer linker (preferably having a length of 18 to 50 amino acid residues), and this results in a particularly flexible structure.

Preferably, the bispecific antibodies contain, in addition to the CD33 antibody according to the invention, an antibody or an antibody fragment that is specific to surface antigens of effector cells, for example, T cells, in particular cytotoxic T cells, NK cells, monocytes, macrophages, dendritic cells or granulocytes. The definition of effector cells in the meaning of the invention comprises all cells of the inherent and adaptive immune system that mediate immune reactions or actively participate therein. It is particularly preferred that these antibodies are specific to the following surface structures on effector cells: CD3, CD8, CD4, CD25, CD28, CD16, NKG2D, NKp46, NKp44, activating KIR receptors (activating killer cell immunoglobulin-like receptors).

An aspect of the invention concerns also antibodies that are conjugated with a ligand that has an effect on the activity of effector cells by binding to the surface of the effector cells. The ligand is selected such that it binds specifically to surface structures of effector cells and, by the binding action, triggers signal cascades for activating the effector cells. Preferably, as a ligand a protein structure or a glycan that binds specifically to a receptor that is specifically expressed on the surface of the effector cells, wherein the ligand by its binding action to the receptor effects activation of the effector cell. It is especially preferred to select the protein structures from ULB-Ps (e.g. ULB-P2), MICA, MICB, as well as cytokines (such as IL2 and IL15) and their fusion proteins.

The connection of the antibody to the further antibody, antibody fragment, or to the protein structure is preferably produced by an expression as a fusion protein or by in vitro methods wherein the further antibodies, antibodies, or protein structures preferably are bonded by linkers such as the peptide linkers to the antibody.

The invention comprises furthermore nucleic acid sequences that code for an antibody according to the invention, as well as vectors that contain the nucleic acid sequences.

The vector (expression vector) is preferably a plasmid, an artificial chromosome; or even a virus particle or another vector that contains an expression cassette that is incorporated stably into the genome of the host (host cell or host organism).

Preferably, the nucleic acid sequences that code for an antibody according to the invention contain the following sequences that code for the CDR regions of the variable regions of the heavy chain:
CDR1 SEQ ID NO. 17,
CDR2 SEQ ID NO. 18,
CDR3 SEQ ID NO. 19, and
the following sequences that code for the CDR regions of the variable regions of the light chains
CDR1 SEQ ID NO. 20,
CDR2 SEQ ID NO. 21, and
CDR3 SEQ ID NO. 22.

It is especially preferred that the nucleic acid sequences that code for an antibody according to the invention contain the following sequences that code for the CDR regions of the variable regions of the heavy chains:
CDR1 SEQ ID NO. 23,
CDR2 SEQ ID NO. 24,
CDR3 SEQ ID NO. 25, and
the following sequences that code for the CDR regions of the variable regions of the light chain
CDR1 SEQ ID NO. 26,
CDR2 SEQ ID NO. 27, and
CDR3 SEQ ID NO. 28.

In a further preferred embodiment of the invention, the nucleic acid sequences that code for an antibody according to the invention contain the following sequence that is coding for the variable region of the heavy chain: SEQ ID NO. 29 and/or the following sequence that codes for the variable region of the light chain: SEQ ID NO. 30.

In yet another preferred embodiment of the invention, the nucleic acid sequences that code for an antibody according to the invention contain the following sequence that is coding for the variable region of the heavy chain: SEQ ID NO. 31 and/or the following sequence that codes for the variable region of the light chain: SEQ ID NO. 32.

Aspects of the invention are also host cells or non-human host organisms that contain a nucleic acid sequence according to the invention.

A host cell is a naturally occurring cell or a transformed or genetically modified cell line or a (multicellular) non-human host organism that contains the expression system according to the invention (i.e., at least one expression vector). The invention comprises in this connection transient transfectants (for example, by mRNA injection), i.e., hosts (host cells or host organisms) in which the expression system is contained as a plasmid or artificial chromosome as well as hosts in which the expression system is integrated stably into the genome of the host (or individual cells of the host). The host cell is preferably selected from prokaryotes or eukaryotes. Preferred prokaryotes are selected from *Escherichia coli* and *Bacillus subtilis*. Preferred eukaryotes are yeast cells (e.g. *Saccharomyces cerevisiae, Pichia pastoris*), insect cells, amphibic cells or mammalian cells, for example, CHO, HeLa, Hek293T, Hek293A. Preferred host organisms are plants, for example, maize or tobacco, invertebrates or vertebrates, in particular *Bovidae, Drosophila melanogaster, Caenorhabditis elegans, Xenopus laevis, Medaka*, zebrafish or *Mus musculus*, or cells or embryos of the aforementioned organisms.

The invention encompasses moreover a pharmaceutical composition that contains one or several antibodies according to the invention in association with a pharmaceutically acceptable dilution agent or carrier. Preferably, the pharmaceutical composition is present in a form suitable for intravenous administration.

Preferably, the composition comprises a chimeric or humanized antibody with a reduced immunogenicity which contains the CDR regions according to the invention.

The pharmaceutical composition according to the invention comprises various administration forms. The pharmaceutical compositions are preferably administered parenterally, particularly preferred intravenously. In one embodiment of the invention, the parenteral pharmaceutical composition exists in an administration form that is suitable for injection. Particularly preferred compositions are therefore solutions, emulsions, or suspensions of the antibody that is present in a pharmaceutically acceptable dilution agent or carrier.

As a carrier, preferably water, buffered water, 0.4% saline solution, 0.3% glycine and similar solvents are used. The solutions are sterile. The pharmaceutical compositions are sterilized by conventional well-known techniques. The compositions contain preferably pharmaceutically acceptable excipients, for example, those that are required in order to provide approximately physiological conditions and/or to increase the stability of the antibody, such as agents for adjusting the pH value and buffering agents, agents for adjusting the toxicity and the like, preferably selected from sodium acetate, sodium chloride, potassium chloride, calcium chloride and sodium lactate. The concentrations of the antibodies according to the invention in these formulations, depending on the application, are variable; they are preferably less than 0.01% by weight, preferably at least 0.1% by weight, further preferred between 1 and 5% by weight and they are selected primarily on the basis of fluid volumes, viscosity etc. or in compliance with the respective administration mode.

The antibodies according to the invention are preferably introduced into a composition that is suitable for parenteral administration. Preferably, the pharmaceutical composition is an injectable buffered solution that contains between 0.1 to 500 mg/ml of antibody, especially preferred between 0.1 to 250 mg/ml of antibody, in particular together with 1 to 500 mmol/l (mM) of a buffer. The injectable solution can be present in liquid as well as a lyophilized administration form. The buffer can be preferably histidine (preferably 1 to 50 mM, especially preferred 5 to 10 mM) at a pH value of 5.0 to 7.0 (especially preferred at a pH of 6.0).

Other suitable buffers encompass, but are explicitly not limited to, sodium succinate, sodium citrate, sodium phosphate, or potassium phosphate. Preferably, sodium chloride between 0 to 300 mM, especially preferred 150 mM, is used for a liquid administration form. For a lyophilized administration form, the pharmaceutical composition contains preferably a cryoprotectant, preferably 0-10% sucrose (especially preferred 0.5-1.0%). Other cryoprotectants comprise trehalose and lactose. For a lyophilized administration form, the pharmaceutical composition contains preferably swelling agents, preferably 1 to 10% mannitol. Other swelling agents encompass glycine and arginine. In liquid as well as lyophilized administration forms, stabilizers are preferably used, especially preferred between 1 to 50 mM of L-methionine (preferably between 5 and 10 mM).

In a preferred embodiment, the pharmaceutical composition comprises the antibody in a dosage quantity of 0.1 mg/kg to 10 mg/kg per administration. Especially preferred dosage quantities comprise 1 mg/kg of body weight.

Pharmaceutical compositions must be sterile and stable under the manufacturing and storage conditions. The composition can be formulated as a solution, microemulsion, dispersion, in liposomes or in other ordered structures that are suitable for high concentrations of antibodies. Sterile injectable solutions can be produced in that the antibody is taken up in the required quantity of the suitable solvents, with one or with a combination of the aforementioned ingredients as needed, followed by sterilization by filtration. For sterile lyophilized powders for producing sterile injectable solutions, the preferred manufacturing methods are vacuum drying and spray drying; this produces a powder of the antibody plus possible additionally desired ingredients from a prior sterile-filtered solution thereof.

The invention comprises the use of the antibody according to the invention as a medication.

The invention comprises further the use of an antibody according to the invention for preparing a medication for therapeutic and/or diagnostic use in case of illnesses that are associated with the expression of CD33, in particular in acute myeloid leukemia (AML).

The invention also encompasses a method for treatment of a human having a disease that is associated with the expression of CD33 by administration of an antibody according to the invention.

The diseases that are associated with the expression of CD33 comprise cancer illnesses such as acute myeloid leukemia (AML), chronic myeloid leukemia (CML), and promyeloid leukemia (PML), and further diseases such as the myelodysplastic syndrome (MDS). The application as a medication comprises also further not explicitly mentioned illnesses that are associated with the expression of CD33.

For therapeutic applications, a sterile pharmaceutical composition, containing a pharmacologically effective quantity of one or several antibodies according to the invention, is administered to a patient in order to treat the aforementioned illnesses.

According to the invention, in particular a use of the antibodies is preferred that leads to targeting of the CD33 expressing cells. For this purpose, by application of the antibody, binding by means of CD33 to the target cells is achieved and killing of the target cells is achieved through the Fc region or through the effector groups on the antibodies. This is realized either by recruiting effector cells or by targeted transport of pharmacological active ingredients (for example, toxins) to the CD33-positive cell and the release thereat.

In a special embodiment of the invention, an antibody in the form of a bispecific antibody is used for treatment of CD33-associated diseases. In this connection, the bispecific antibody in an especially preferred embodiment of the invention comprises an scFv fragment according to the invention and an scFv fragment that is specific to a surface structure of NK cells, preferably against ULB-P2. Preferably, the bispecific antibody is used for treatment of AML.

In a further especially preferred embodiment of the invention, the bispecific antibody contains an scFv fragment according to the invention and an scFv fragment that is specific to the surface structure of T cells, preferably against CD3 or CD8. Preferably, the bispecific antibody is used for treatment of AML.

In addition to the use in the medical field for therapeutic purposes, the antibodies according to the invention are suitable for diagnostics, biological research, and other applications in which the detection of CD33 is of interest. Such applications are in particular Western blot, immunostaining of cells (for example, for flow cytometry and microscopy), and ELISA.

The invention also encompasses a method for preparing an antibody according to the invention, in which a host cell or non-human host organism is exposed to conditions that are favorable for the expression and optionally secretion of the antibody, and optionally purifies at least partially the antibody. Preferably, for this purpose, host cells are cultivated in a selective medium that selects with regard to the growth of the cells that contain an expression vector. The expression of the gene sequences of the expression vector results in the production of the antibodies or fusion proteins. The expressed antibodies or fusion proteins are then isolated and purified by any conventional method, including extraction, precipitation, chromatography, electrophoresis, but also by affinity chromatography.

The antibodies according to the invention are endocytosed only slowly by CD33-positive cells (FIG. 7). This has the advantage that the antibodies according to the invention or the antibody fragments in a therapeutic application stay for an extended period of time on the surface of the CD33-positive cells. In this way, they are accessible for a long period of time for effector cells that, in turn, mediate the immune reaction against the CD33-positive cells (target cells). This increases the effectiveness of a therapy. Antibodies that are quickly endocytosed are not suitable for such an application. Accordingly, because of these special properties, the antibodies according to the invention are distinguished from the antibodies known from the prior art. In addition to their high affinity to CD33, they offer the possibility of an effective therapeutic application whose action mechanism is based on recruiting effector cells.

BRIEF DESCRIPTION OF THE DRAWINGS

The invention will be explained in more detail based on the following Figures and embodiments without limiting the invention to them.

Figures

FIG. 1 shows a sequence comparison of the CDR regions of two antibodies according to the invention, anti-CD33DRB1 and anti-CD33DRB2, with the CDR regions of the variable regions of the light and heavy chains of the anti-CD33 antibodies known in the prior art. Illustrated is also the percentage of sequence identity (% SI) of the amino acid sequences to the sequences according to the invention.

DESCRIPTION OF PREFERRED EMBODIMENTS

Example 1

Figure 2:
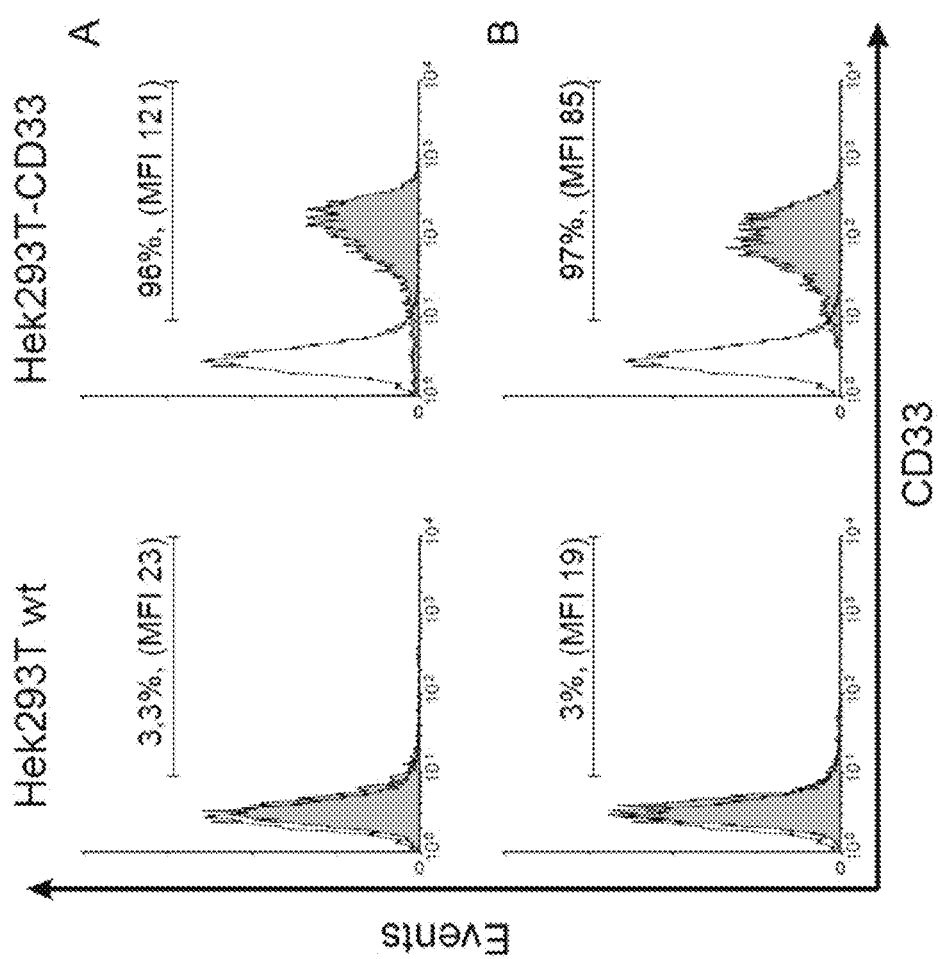
FIG. 2 shows binding of two anti-CD33DRB antibodies of the supernatant of the hybridomas on CD33-Hek293T cells. In this connection, (A) shows binding of an antibody with the CDR regions of the anti-CD33DRB1. (B) shows binding of an antibody with the CDR regions of the anti-CD33DRB2. Illustrated is the median fluorescence intensity (MFI) of the flow cytometry analysis wherein, to the left, binding on wild type cells Hek293T cells (wt) and, to the right, binding to the CD33$^+$-Hek293T cells (Hek293T-CD33) is illustrated.

Preparation and Characterization of Monoclonal Murine anti-CD33DRB Antibodies

For preparing new anti-CD33 antibodies, the murine fibroblast cell line A9 (ATCC CCL-1.4, American Type Culture Collection, Rockville, Md., U.S.A.) was transduced stably with human CD33. With the thus obtained cells, three mice were immunized. After immunization, sera of the immunized mice were applied to with Hek293T cells (ATCC CRL-11268) that were also transduced with human CD33 (CD33+-Hek293T cells) in various degrees of dilution and immunofluorescence staining was carried out. The serum of the mouse #3 showed at the highest dilution of 1:1,000 significantly the highest reactivity so that the splenocytes of this mouse were used for the hybridoma fusion. Accordingly, the murine myeloma cell line X63Ag8.653 (ATCC CRL 1580) was fused in the logarithmic growth phase with splenocytes of the mouse #3 and subsequently cultured in a selection medium (HAT medium). After two weeks of culturing, the antibody production of the hybridomas was tested. Two hybridomas were identified that are characterized by an especially high affinity to CD33 (anti-CD33DRB1 and anti-CD33DRB2).

Sequencing of the variable regions of the light and heavy chains show the following sequences:
anti-CD33DRB1: $V_H$ a sequence according to SEQ ID NO. 31, $V_L$ a sequence according to SEQ ID NO. 32, and
anti-CD33DRB2: $V_H$ a sequence according to SEQ ID NO. 29, $V_L$ a sequence according to SEQ ID NO. 30.

The CDR regions of the variable regions of the light and heavy chains have the following gene sequences:
anti-CD33DRB1: $V_H$: CDR1 a sequence according to SEQ ID NO. 23, CDR2 a sequence according to SEQ ID NO. 24, CDR3 a sequence according to SEQ ID NO. 25; $V_L$: CDR1 a sequence according to SEQ ID NO. 27, CDR2 a sequence according to SEQ ID NO. 28, CDR3 a sequence according to SEQ ID NO. 29 and
anti-CD33DRB2: $V_H$: CDR1 a sequence according to SEQ ID NO. 17, CDR2 a sequence according to SEQ ID NO. 18, CDR3 a sequence according to SEQ ID NO. 19; $V_L$: CDR1 a sequence according to SEQ ID NO. 20, CDR2 a sequence according to SEQ ID NO. 21, CDR3 a sequence according to SEQ ID NO. 22.

They code for the following amino acid sequences that contain the specific CDR regions:
anti-CD33DRB1: $V_H$ a sequence according to SEQ ID NO. 15, $V_L$ a sequence according to SEQ ID NO. 16, and
anti-CD33DRB2: $V_H$ a sequence according to SEQ ID NO. 13, $V_L$ a sequence according to SEQ ID NO. 14,
and the CDR regions of
anti-CD33DRB1: $V_H$: CDR1 a sequence according to SEQ ID NO. 7, CDR2 a sequence according to SEQ ID NO. 8, CDR3 a sequence according to SEQ. ID NO. 9; $V_L$: CDR1 a sequence according to SEQ ID NO. 10, CDR2 a sequence according to SEQ ID NO. 11, CDR3 a sequence according to SEQ ID NO. 12, and
anti-CD33DRB2: $V_H$: CDR1 a sequence according to SEQ ID NO. 1, CDR2 a sequence according to SEQ ID NO. 2, CDR3 a sequence according to SEQ ID NO. 3; $V_L$: CDR1 a sequence according to SEQ ID NO. 4, CDR2 a sequence according to SEQ ID NO. 5, CDR3 a sequence according to SEQ ID NO. 6.

The amino acid sequences of the CDR regions of the two antibodies according to the invention differ significantly from anti-CD33 antibodies (FIG. 1) known up to now.

Figure 3:
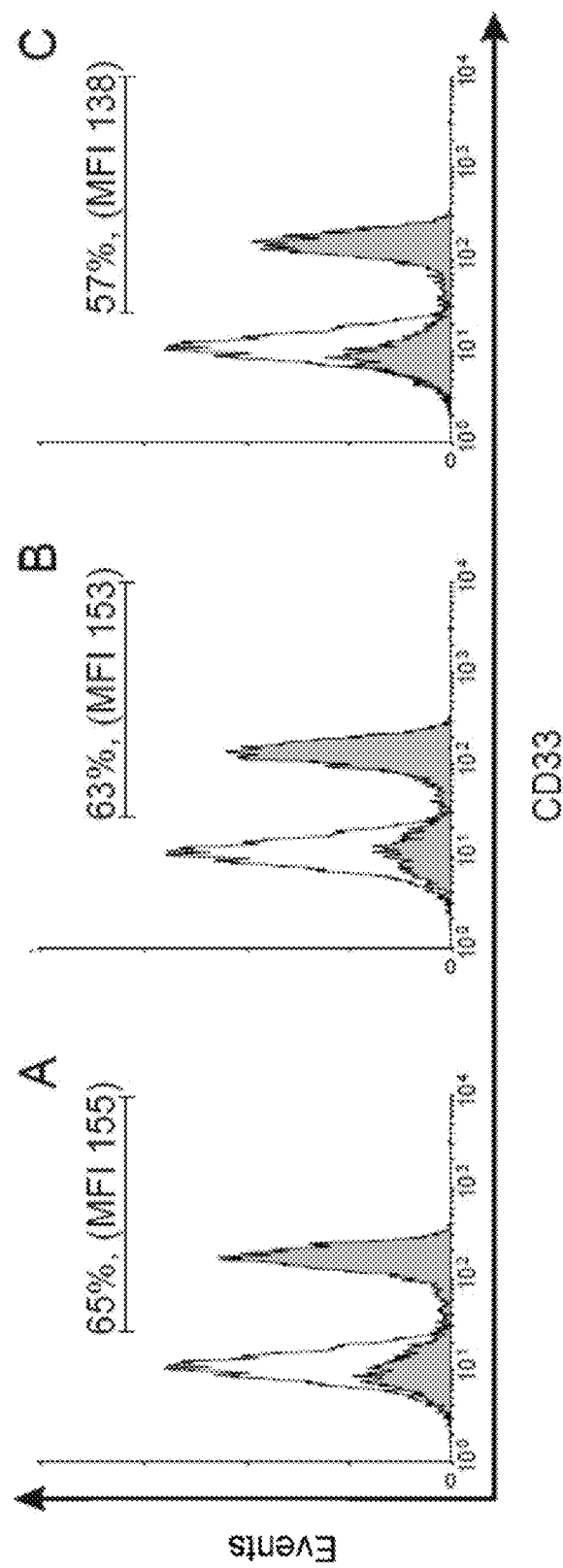
FIG. 3 shows binding of anti-CD33 antibodies to HL60 cells. (A) shows in this context binding of a commercial anti-CD33 antibody, (B) shows binding of the antibody with the CDR regions of anti-CD33DRB1, and (C) shows binding of the antibody with CDR regions of anti-CD33DRB2. Illustrated is the mean fluorescence intensity (MFI) of the flow cytometry analysis.

Binding of the antibodies from the hybridoma supernatants on CD33+-Hek293T cells and on the CD33+ human cell line HL60 was verified by FACS analyses (FIGS. 2 and 3).

For providing monoclonal antibodies from the hybridoma cells, the latter were recloned.

Example 2

Preparation of an scFv Construct of anti-CD33DRB2

The coding areas of the heavy and light chains of the variable regions of the antibodies anti-CD33DRB2 from Example 1 were amplified with specific primers and cloned into a pSecTag2B vector for expression in eukaryote cells. In order to test the binding strength of the scFv (single chain variable fragments), the latter were expressed in Hek293T cells. For this purpose, the vector (pSecTag2B containing the coding areas) was transformed into *E. coli* Top10F bacteria and the plasmids prepared. The obtained expression vectors that code for the scFv antibodies were introduced by transfection with polyethylene imine (PEI) into Hek293T cells. After culturing the transfected cells for five days, the supernatant was removed and the antibodies were purified.

Figure 4:
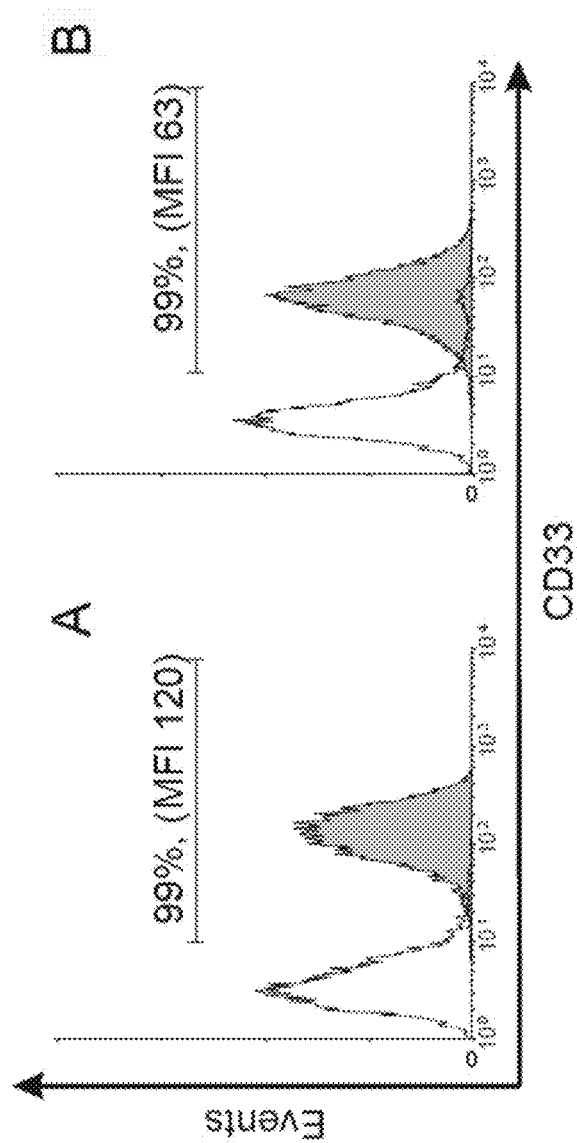
FIG. 4 shows the comparison of binding of (A) monoclonal anti-CD33DRB1 and (B) of an scFv fragment with the CDR regions of the anti-CD33DRB2 on CD33+-Hek293T cells. Illustrated is the mean fluorescence intensity (MFI) of flow cytometry analysis.

The obtained scFv antibodies, in the following referred to as anti-CD33DRB2 scFv, were tested by immunofluorescence staining with respect to their binding to CD33+-Hek293T cells and compared with the monoclonal anti-CD33DRB2 (FIG. 4). The monoclonal antibody as well as the scFv antibody exhibited a comparable binding action to CD33+-Hek293T cells wherein the number of bonded cells was identical, but the binding strength that is expressed by the mean fluorescence intensity was slightly reduced for the scFv antibody. This can be explained in that the scFv antibody binds only with one pair of variable region of the light and heavy chain to the antigen.

Example 3

Preparation of Different Bispecific CD3×CD33 Antibodies and Immunotargeting of T Cells For use as a targeting construct for targeting CD33+ cells, a bispecific antibody (single chain bispecific diabody, scBsDb) was produced that bind with one arm on CD33 and with the other arm on CD3. The domain that binds to CD33 contains the variable region of the anti-CD33DRB2 of Examples 1 and 2. It serves for binding to the target cells, for example, tumor cells. The other domain binds to CD3, a component of the T cell receptor complex, and serves for activation of T cells. In this way, recruiting of T cells on the target cells is enabled and permits in this way combating of the target cells by the T cells.

For producing the antibodies, an outer cassette for the first antibody, containing the variable region of the heavy chain ($V_H$) which is positioned proximal to the variable region of the light chain ($V_L$), wherein $V_H$ and $V_L$ are connected by a glycine-serine linker of $(Gly_4Ser)_3$. The inner cassette contains the sequence of the variable regions of light and heavy chain of the second antibody in reversed form and a glycine-serine linker of $(Gly_4Ser)_5$ in order to ensure correct folding of scBsDb. In this way, two different bispecific antibodies were produced which differ in the arrangement of variable regions of the anti-CD33 and anti-CD3 antibodies.

CD33×CD3 scBsDb (outer cassette CD3-inner cassette CD3):

CD33×CD3 scBsDb (outer cassette CD3-inner cassette CD33):

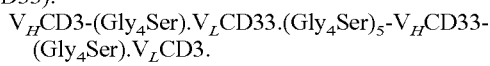

The coding sequences of the CD33×CD3 scBsDb and CD3×CD33 scBsDb were cloned into a retroviral pcz-CFG 5.1 vector. The two constructs were introduced into a packaging cell line and the obtained viral particles were introduced into Hek293T cells where their coding sequence was introduced stably into the genome and in this way stable cell lines were obtained that express the two antibodies, CD33× CD3 scBsDb and CD3×CD33 scBsDb. The latter were purified by Ni-NTA column.

The thus obtained bispecific antibodies contained in addition to the complete form a further 37 kDa size product which most likely was produced by proteolysis and has a significant negative effect on the cytotoxicity. The cytotoxicity was determined by $^{51}Cr$ release assay with $^{51}Cr$-CD33+-Hek293T cells. CD33×CD3 scBsDb and CD3×CD33 scBsDb in in vitro co-cultures of CD33+-Hek293T cells and PBMC achieved a specific T cell mediated lysis of the CD33+-Hek293T cells of 27% or 23%.

Example 4

Figure 5:
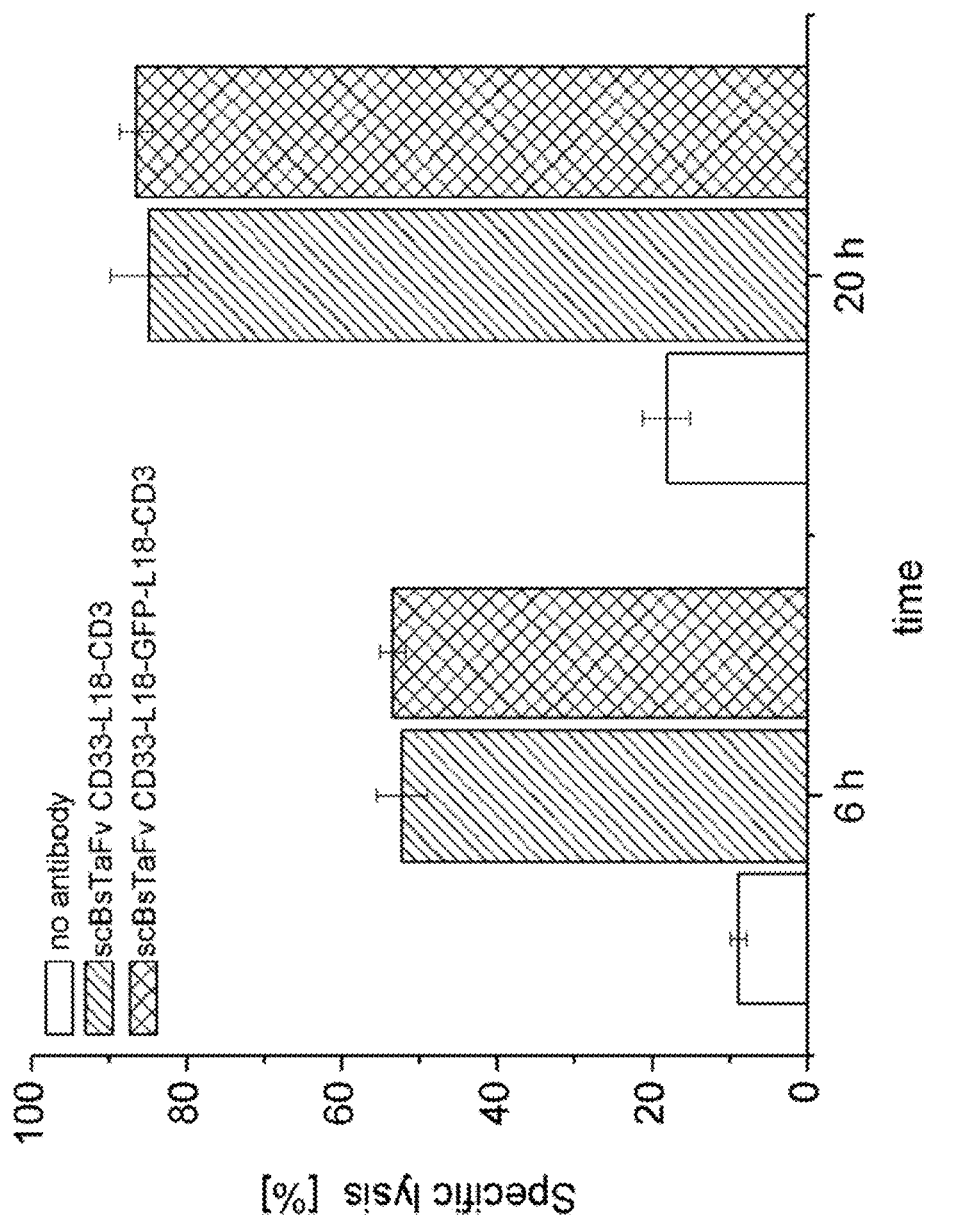
FIG. 5 shows the T cell-mediated specific lysis of CD33+-Hek293T cells which is controlled by two different scBsTaFv that are specific to CD33 (with the CDR regions of the anti-CD33DRB2) and CD3. Illustrated is the proportion of the CD33+-Hek293T cells that are affected by the lysis that is mediated by the T cells.

Preparation of CD3×CD33 Tandem Antibodies (scBsTaFv) and Immunotargeting of T cells In order to further increase the T cell mediated cytotoxicity, tandem antibodies with larger linker structures were constructed in order to avoid proteolysis. In the bispecific tandem antibodies (scBsTaFv) the variable regions of the anti-CD33 antibody and the anti-CD3 antibody are arranged on a polypeptide chain wherein the two scFv fragments are linked with a linker of a length of 18 amino acids for proper folding. A further construct contained in addition to the L18 also the green-fluorescent protein (GFP). Both constructs, CD33-L18-CD3 and CD33-L18-GFP-L18-CD3, were expressed and purified in analogy to Example 3. The cytotoxicity was also determined in analogy to Example 3 with a $^{51}Cr$ release assay (FIG. 5). The specific lysis of the CD33+-Hek293T cells for these antibody constructs is up to 86% for a 20-hour in vitro culture.

Example 5

Preparation of ULB-P2×CD33 Tandem Antibodies (scBsFv) and Immunotargeting of NK. Cells In order to achieve immunotargeting of NK cells, tandem antibodies were constructed that contain CD33 and ULB-P2. ULB-P2 is the ligand of the activated NK cell receptor NKG2D. By combination of an activating ligand and an anti-CD33 scFv antibody in a tandem antibody, immunotargeting of NK cells on CD33+ target cells is mediated. The construct of the tandem antibody contains ULB-P2, a short $(Gly_4Ser)$ linker, and the $V_H$ and $V_L$ regions of the anti-CD33DRB2 that are linked by a long linker structure $(Gly_4Ser)_3$ as well as a Myc tag and six His tags for purification. The antibodies were introduced in analogy to Examples 3 and 4 into an expression vector, expressed and purified.

Figure 6:
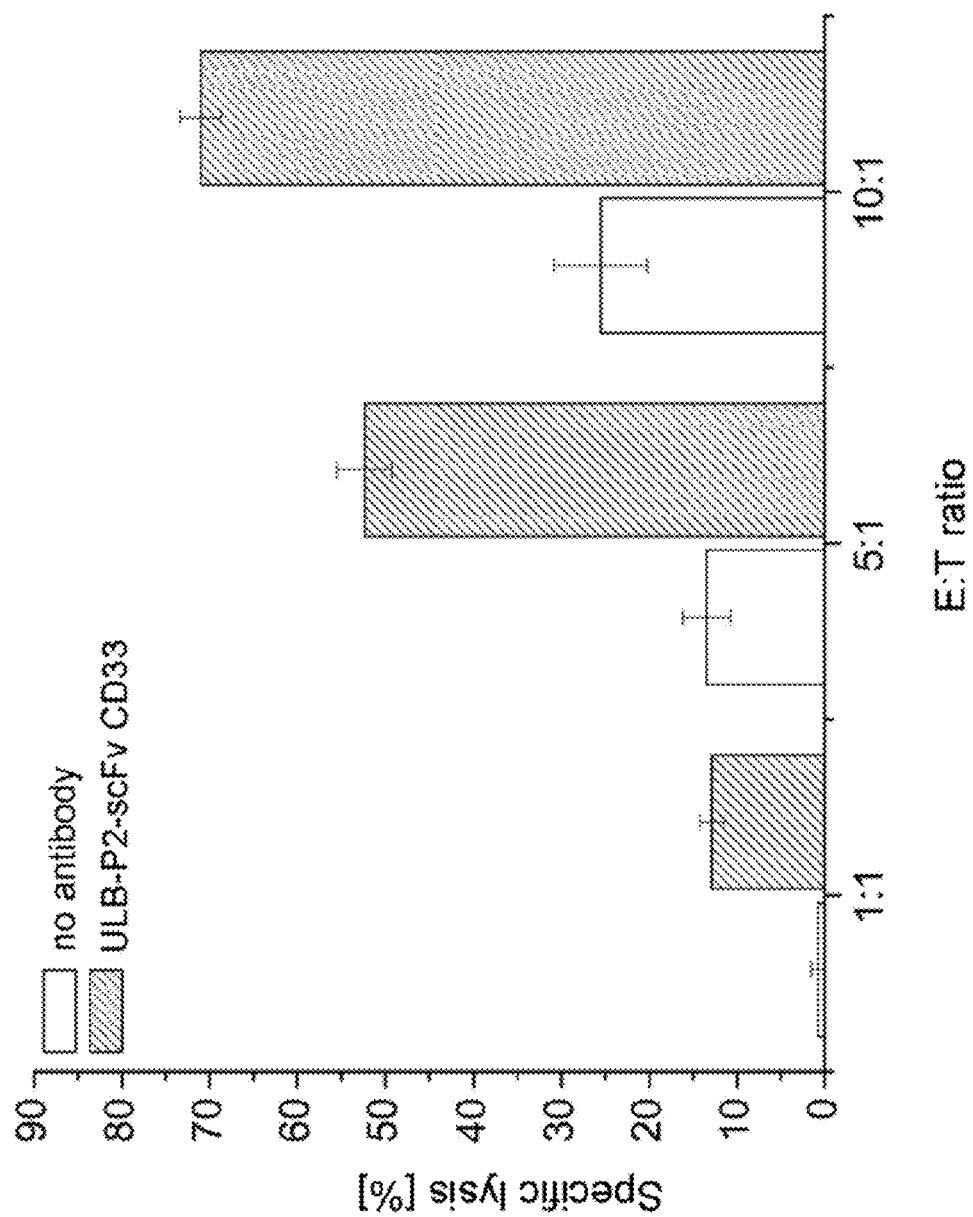
FIG. 6 shows the NK cell-mediated specific lysis of CD33+-P815 cells which is controlled by a bispecific recombinant protein of ULB-P2 and scFv CD33 (with the CDR regions of the anti-CD 3DRB2. Illustrated is the proportion of the CD33+-Hek293T cells that are affected by the NK cell-mediated specific lysis. The experiments were carried out in different ratios between effector cells (NK cells) and target cells (CD33+-P815 cells) (E:T ratio, ratio effector cells to target cells).

The NK cell-mediated cytotoxicity was determined by $^{51}Cr$ release assay in CD33+-P815 (ATCC TIB-6) (FIG. 6). In the presence of the tandem antibody, a significantly increased NK cell-mediated cytotoxicity was determined.

Example 6

Anti-CD33 Antibodies According to the Invention are Endocytosed only Weekly by Cancer Cells It is desirable that in a therapeutic treatment of CD33-associated illnesses, for example, acute myeloid leukemia (AML), the residence time of the antibodies used for therapy on the cell surface is high. This has the effect that effector cells can be effectively recruited on the cancer cells. In case of a rapid endocytosis of the antibodies by the cancer cells, the binding sites for the effector cells would no longer be accessible after a short period of time and targeting of the effector cells would therefore be less effective.

Figure 7:
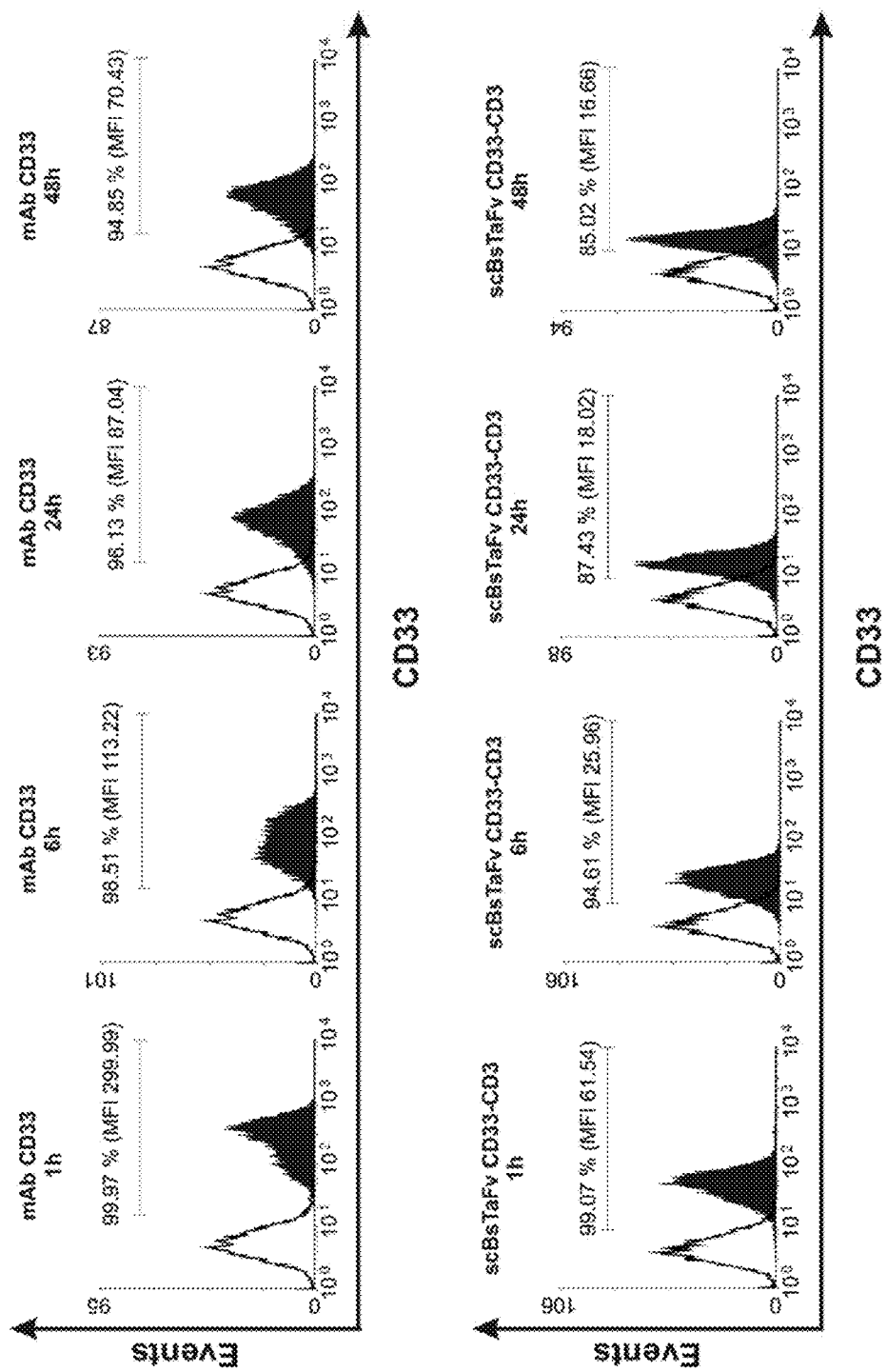
FIG. 7 shows the residence time of the anti-CD33 antibodies according to the invention on the surface of CD33-positive blasts of a leukemia patient with AML. At the top: binding of anti-CD33DRB2 (from Example 1), at 1, 6, 24 and 48 hrs after incubation with the CD33-positive blasts (black), respectively. The detection was realized by staining with PE-marked anti-murine IgG antibody (white: negative control without anti-DC33 antibody). Bottom: binding of CD3× CD33 scBsTaFv (from Example 4), at 1, 6, 24, and 48 hrs after incubation with CD33-positive blasts (black), respectively. The detection was realized by staining with PE-marked anti-myc antibody (white: negative control without CD 3×CD33 scBsTaFv).

In order to demonstrate that the antibodies according to the invention are endocytosed only at a minimal rate by the CD33-positive cancer cells, CD33-positive blasts of leukemia patients were incubated at 4 degrees C. for 1 hr with a monoclonal anti-CD33DRB2 antibody (as disclosed in Example 1) or with a CD3×CD33 scBsTaFv tandem antibody (as disclosed in Example 4). By FACS analysis, the presence of the anti-CD33 antibodies on the surface of the CD33-positive blasts was detected in that staining of the anti-CD33 antibodies was performed with a PE-marked anti-murine IgG antibody (for the monoclonal anti-CD33DRB2, FIG. 7 at the top, black histogram) or with a PE-marked anti-myc antibody (for the tandem antibody, FIG. 7 at the bottom, black histogram). In parallel, as a negative control without incubation with anti-CD33 antibodies, CD33-positive blasts of the same patient, were stained with the same antibodies, respectively (FIG. 7, white histogram, respectively).

Even 48 hours after contacting with the CD33-positive blasts, the antibodies could be detected on the surface. The antibodies, the monoclonal antibody as well as the bispecific antibody derivative, were predominantly not endocytosed during this time by the CD33-positive blasts. It is thus ensured for 48 hrs that the antibodies are present for 48 hrs on the surface of the cells to be killed and therefore, over an extended period of time, are capable of serving for recruiting and binding effector cells (in case of the monoclonal antibodies, for example, by means of Fc receptors; in case of the bispecific antibody derivatives by specific binding of the further antibodies).

What is claimed is:

1. An isolated monoclonal anti-CD33 antibody containing six complementary determining regions (CDRs), characterized in that the six CDRs comprise the following sequences:
   a) variable region of heavy chain ($V_H$)
   CDR1 DYVVH (SEQ ID No. 1),
   CDR2 YINPYNDGTKYNEKFKG (SEQ ID No. 2),
   CDR3 DYRYEVYGMDY (SEQ ID No. 3),
   and
   b) variable region of light chain ($V_L$)
   CDR1 TASSSVNYIH (SEQ ID No. 4),
   CDR2 TSKVAS (SEQ ID No. 5),
   CDR3 QQWRSYPLT (SEQ ID No. 6).

2. The antibody according to claim 1, containing the following structure:
   a heavy chain variable region with the sequence of SEQ ID NO. 13
   and a light chain variable region with a sequence of SEQ ID NO. 14.

3. The antibody according to claim 1, containing additionally at least one of the following structures
   a constant region of a heavy chain of a human IgG,
   a constant region ($C_L$) of the human kappa light chain and/or
   a human IgG3 hinge region,
   optionally in the form of a F(ab')$_2$ fragment.

4. The antibody according to claim 1 in the form of an scFv fragment or in the form of a F(ab')$_2$ fragment.

5. The antibody according to claim 1, characterized in that it is conjugated with an effector group or a further antibody or antigen binding fragment that is specific to another antigen than CD33.

6. The antibody according to claim 5, wherein the effector group is selected from toxins, enzymes, co-stimulating molecules, radionuclides and nucleic acids.

7. The antibody according to claim 1, characterized in that it is conjugated with a ligand that binds specifically to effector cells and in this way affects their activity.

8. An isolated nucleic acid coding for an antibody of claim 1.

9. A vector containing a nucleic acid sequence of claim 8.

10. An isolated host cell containing a nucleic acid of claim 8 or a vector containing a nucleic acid of claim 8.

11. A pharmaceutical composition, containing an antibody of claim 1 in association with a pharmaceutically acceptable dilution agent or carrier.

12. A method for preparing an antibody of claim 1, in which:
   a. an isolated host cell that contains a nucleic acid coding for an antibody of claim 1 or that contains a vector containing a nucleic acid coding for an antibody of claim 1 is exposed to conditions under which an expression and optionally a secretion of the antibody takes place, and
   b. the antibody is at least partially purified.

13. The antibody according to claim 1 wherein the antibody is a humanized antibody.

14. The antibody according to claim 5, wherein the connection of the antibody to the effector group is prepared by the expression as a fusion protein.

* * * * *